United States Patent [19]
Odioso et al.

[11] 3,946,945
[45] Mar. 30, 1976

[54] DISPENSING CONTAINER AND REFILL FOR AN AIR TREATING GEL

[75] Inventors: Raymond C. Odioso, Cincinnati, Ohio; William T. Riley, Harrison, Ind.; David A. Jones, Bellbrook, Ohio

[73] Assignee: The Drackett Company, Cincinnati, Ohio

[22] Filed: July 14, 1975

[21] Appl. No.: 595,460

[52] U.S. Cl. .......................... 239/58; 206/.5; 239/60
[51] Int. Cl.² ...................... A24F 25/00; A61L 9/04
[58] Field of Search .............................. 239/53–60; 206/.5

[56] References Cited
UNITED STATES PATENTS

| | | | |
|---|---|---|---|
| 2,765,950 | 10/1956 | Wheeler | 239/58 X |
| 2,765,951 | 10/1956 | Wheeler | 239/58 X |
| 3,134,544 | 5/1964 | Copley | 239/55 |
| 3,575,346 | 4/1971 | Roth et al. | 239/55 X |
| 3,770,199 | 11/1973 | Hock et al. | 239/54 |

*Primary Examiner*—Robert S. Ward, Jr.
*Attorney, Agent, or Firm*—David J. Mugford; George A. Mentis; Samuel J. DuBoff

[57] ABSTRACT

A dispensing container for an air treating gel comprising: (A) a base member of relatively flat and circular contour having a raised circular gel-supporting surface having a first stem located at the center of the surface projecting vertically upward therefrom, said first stem having a relatively short upper portion having a substantially smaller diameter than the remaining longer lower portion, said surface having a cylindrical side wall providing a lip portion about the circumference of said surface, said wall being integrally connected at its lowermost portion to the lowermost portion of a second cylindrical wall laterally offset therefrom to provide an annular recess about the circumference of said surface; (B) a top member of relatively flat and circular contour having a cylindrical side wall disposed about its circumference, said top member having a second central hollow stem for insertion therein of the upper portion of said first stem; and (C) a tubular-walled member capable of slideably engaging the outer surface of the top side wall member while the base member first stem and top member second stem remain fixedly engaged, whereby the vertical displacement of the lowermost edge of said tubular-walled member relative to the base member can be varied to obtain a plurality of open positions and can be adjusted to a fully closed position when said edge is caused to be inserted into said annular recess to provide a vapor-tight seal. Additionally, the dispensing container is capable of functioning as a refill for a room deodorizer having a bottom portion of generally cylindrical shape and a closure of generally frusto-conical shape which is adjustable with respect to the bottom by means of a mating hollow bottom post and closure post which frictionally engages the inner surface of the hollow bottom post.

5 Claims, 3 Drawing Figures

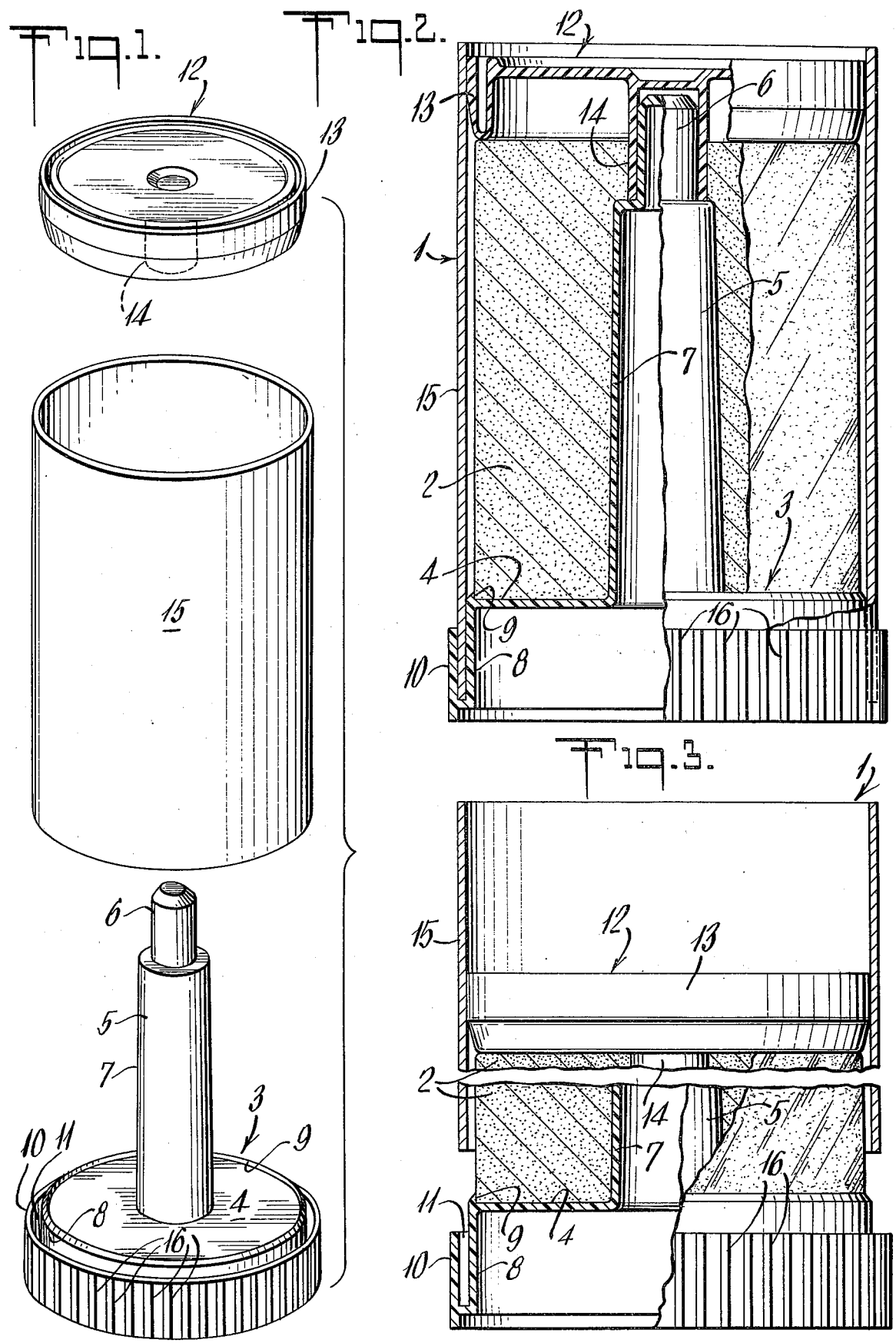

DISPENSING CONTAINER AND REFILL FOR AN AIR TREATING GEL

BACKGROUND OF THE INVENTION

This invention relates to dispensing containers for evaporative air treating gels wherein the container is additionally capable of functioning as a refill for a room deodorizer having a base and a closure portion, the position of which relative to the base is adjustable by means of frictionally engaging vertical posts projecting towards each other from inside the closure and inside the base.

Air treating gels such as disclosed in U.S. Pat. No. 2,691,615 to Turner et al. provide the desirable effect of gradual introduction into the surrounding atmosphere such as in a room in a residential house, of volitalizable air treating components which includes, for example, air freshening and odor treating components. Along with this desirable effect has followed a great demand on the part of consumers for various types of devices which are capable of dispensing such air treating gels. Many types of dispensers are now available commercially and have been disclosed in patent literature such as, for example, in U.S. Pat., No. D224,783 to Jones, Nos. 3,239,145 and 2,878,060 to Russo, Nos. 2,765,950 and 2,765,951 to Wheeler, No. 2,783,084 to Paxton, No. 3,857,512 to Levey and No. 3,104,816 to Jaffee.

Additionally, and up to most recently, the majority of such room deodorizer dispensers have been attractively packaged but have of necessity required disposal thereof once the air treating gel contained therein became dissipated (e.g., after about 1–2 months). However, consumers have found the deodorizing dispensers attractive and, therefore, have been desirous of being able to reuse such dispensers if a refill were available. Concurrently, many consumers have also expressed a desire for using a room deodorizer dispenser which would be substantially less costly than those currently available commercially.

Therefore, a great demand has arisen for an economical room deodorizer dispenser which would additionally be capable of functioning as a refill for more decorative dispensers currently available commercially. Specifically, there has heretofore not been available such a dispenser which is additionally capable of functioning as a refill for an air freshener container of the type disclosed in U.S. Pat. No. D224,783 to Jones. This patented dispenser is capable of containing therein a cake of an air treating deodorizing gel and is comprised of a bottom portion of generally cylindrical shape having a flat circular gel-supporting surface at the axial center from which upwardly projects a first hollow vertical post, and a generally frusto-conically shaped closure portion having at its axial center a second vertical post projecting downwardly therefrom, wherein a portion of the outer surface of the second post is capable of frictionally engaging the inner surface of the first post to provide a plurality of height displacements of the lowermost edge of the closure relative to the bottom.

DESCRIPTION OF THE DRAWINGS

FIG. 1 is an exploded view of the dispensing container which is capable of functioning as a refill.

FIG. 2 is a front sectional view of the container of FIG. 1 with the tubular-walled member in closed position over the base member with portions of the structure broken away and in section to show the details thereof.

FIG. 3 is a front sectional view of the container of FIG. 1 with the tubular-walled member in an open position displaced from the base member to expose the air treating gel with portions of the structure broken away and in section to show the details thereof.

DESCRIPTION OF THE PREFERRED EMBODIMENT

Referring to FIG. 1, the dispensing container 1 capable of functioning as a refill for a room deodorizer such as is disclosed in U.S. Patent No. D224,783 for containing an air treating gel is comprised of three basic elements: a base member 3, a top member 12 and a tubular-walled member 15. As is shown in FIGS. 2 and 3, base member 3 is relatively flat and of circular contour having a raised circular surface 4 for supporting a cake of air treating gel 2 and having a first stem 5 located at the axial center of the surface projecting perpendicularly or vertically upward therefrom. This first stem has a relatively short upper portion 6 having a substantially smaller diameter than the remaining longer lower portion 7. The surface 4 also has a cylindrical side wall 8 which projects slightly upwardly providing a lip portion 9 about the circumference of the surface. The wall 8 is additionally integrally connected at its lowermost portion to the lowermost portion of a second cylindrical wall 10 laterally offset therefrom to provide an annular recess 11 between the walls and about the circumference of surface 4.

The top member 12 is of relatively flat and circular contour having a cylindrical side wall 13 disposed about its circumference. Top member 12 additionally has a second central hollow stem 14 projecting vertically downwardly at the axial center of the top member 12 for insertion therein of the upper portion 6 of the first stem 5.

The lowermost edge of tubular-walled member 15 is capable of being removably inserted into annular recess 11 to provide a vapor-tight seal when the container 1 is in the closed position. The inner surface of member 15 is capable of slideably engaging the outer surface of the side wall 13 of the top member 12 while the first stem 5 of base member 3 and the second stem 14 of top member 12 remain fixedly engaged thereby allowing vertical displacement of the lowermost edge of tubular-walled member 15 relative to the base member 3 to obtain a plurality of open positions for varying degrees of exposure of the air treating gel 2 contained in container 1.

Preferably, the uppermost edge of second wall 10 in the base member 3 is at a lower level in space relation to the level of surface 4 and lip portion 9 to aid in preventing pieces of gel from becoming dislodged from the cake of air treating gel 2 as a result of movement of tubular-walled member 15 during use as a dispenser. Also, a plurality of vertically spaced-apart projections 16 may be provided about the outer surface of second wall 10 to provide a knurling effect to aid the user in gripping base member 3 while displacing tubular-walled member 15 a vertical distance therefrom for activation of the air treating gel 2.

To prevent premature evaporation or dissipation of the gel during storage or non-use, tubular-walled member 15 is preferably composed of a laminated structure comprising an inner layer of polypropylene film, a middle layer of aluminum foil and an outer layer of spirally-wound Kraft paper. Plastic films other than polypropylene can be utilized which are not chemically reactive with the air treating gel, such as polyethylene film. Such laminated structures are well known and are similar to those disclosed in U.S. Pat. Nos. 3,572,499 to Mondano, 3,315,864 to Martin et al and 3,147,902 to Miller. The thickness of each of the polypropylene film and the aluminum foil should be adequate to provide an effective vapor barrier for the gel and can be from 1–3 mils, and is preferably about 1 mil. The Kraft paper need be thick enough to provide rigidity to the tubular structure.

Another aspect of the invention is the use of container 1 as an economical refill for a room deodorizer of the type disclosed in U.S. Patent No. D224,783. To be used as a refill, the user grasps the outer surface of second wall 10 of base member 3 while lifting the outer surface of tubular-walled member 15 while simultaneously disengaging second stem 14 of top member 12 from the upper portion 6 of first stem 5 of the base member 3. The bottom portion of the room deodorizer is inverted and the hollow post projecting vertically along the axial center thereof is inserted over the upper portion 6 of stem 5 to interlock therewith. The interlocked combination is then inverted and the gel cake is gently squeezed if necessary to enable the cake to slide down the hollow post and onto the room deodorizer bottom portion surface. The refill base member stem 5 is disengaged from the room deodorizer hollow post, and the closure portion of the room deodorizer is replaced over the bottom portion making the deodorizer ready for use once more.

What is claimed is:

1. A dispensing container for an air treating gel comprising:
  A. a base member of relatively flat and circular contour having a raised circular gel-supporting surface having a first stem located at the center of the surface projecting vertically upward therefrom, said first stem having a relatively short upper portion having a substantially smaller diameter than the lower portion, said surface having a cylindrical side wall providing a lip portion about the circumference of said surface, said wall being integrally connected at its lowermost portion to the lowermost portion of a second cylindrical wall laterally offset therefrom to provide an annular recess about the circumference of said surface;
  B. a top member of relatively flat and circular contour having a cylindrical side wall disposed about its circumference, said top member having a second central hollow stem for insertion therein of the upper portion of said first stem; and
  C. a tubular-walled member capable of slideably engaging the outer surface of the top side wall member while the base member first stem and top member second stem remain fixedly engaged, whereby the vertical displacement of the lowermost edge of said tubular-walled member relative to the base member can be varied to obtain a plurality of open positions and can be adjusted to a fully closed position when said edge is caused to be inserted into said annular recess to provide a vapor-tight seal.

2. The container of claim 1 wherein the uppermost edge of said second wall is at a lower level in space relation to the level of said surface.

3. The container of claim 1 wherein the outer surface of said second wall contains a plurality of vertically spaced-apart projections disposed about the circumference of said wall.

4. The container of claim 1 wherein said tubular-walled member is composed of a laminated structure comprising an innner layer of polypropylene film, a middle layer of aluminum foil, and an outer layer of spirally-wound Kraft paper.

5. A refill for a room deodorizer wherein a cake of an air treating deodorizing gel is disposed therein and comprised of a bottom portion of generally cylindrical shape having a flat circular gel-supporting surface at the axial center of which upwardly projects a first hollow vertical post and a generally frusto-conically shaped closure portion having at its axial center a second vertical post projecting downwardly therefrom, wherein a portion of the outer surface of said second post is capable of frictionally engaging the inner surface of said first post to provide a plurality of height displacements of the lowermost edge of the closure relative to the bottom, said refill being capable of functioning additionally as a dispensing container for said air treating gel and comprising:
  A. a base member of relatively flat and circular contour having a raised circular gel-supporting surface having a first stem located at the center of the surface projecting vertically upward therefrom, said first stem having a relatively short upper portion having a substantially smaller diameter than the remaining longer lower portion, said stem upper portion being capable of interlocking with said first post, said surface having a cylindrical side wall providing a lip portion about the circumference of said surface, said wall being integrally connected at its lowermost portion to the lowermost portion of a second cylindrical wall laterally offset therefrom to provide an annular recess about the circumference of said surface;
  B. a top member of relatively flat and circular contour having a cylindrical side wall disposed about its circumference, said top member having a second central hollow stem for insertion therein of the upper portion of said first stem;
  C. a tubular-walled member capable of slideably engaging the outer surface of the top side wall member while the base member first stem and top member second stem remain fixedly engaged, whereby the vertical displacement of the lowermost edge of said tubular-walled member relative to the base member can be varied to obtain a plurality of open positions and can be adjusted to a fully closed postiion when said edge is caused to be inserted into said annular recess to provide a vapor-tight seal;
  D. a cylindrically-shaped cake of air treating deodorizing gel disposed on said base member surface within the confines of said lip portion, said cake having a hollow portion at its axial center of substantially the same diameter and height as the lower portion of the first stem, wherein additionally the diameter of the cake is slightly less than the diameter of said room deodorizer bottom portion surface and the height of said cake is less than the height of said closure portion, whereby when said refill base member containing said cake of air treating gel is placed on a horizontal surface, the hollow post of the room deodorizer bottom portion placed over the upper portion of the base member stem to interlock therewith, and the interlocked combination inverted, the cake will slide down the hollow post onto the bottom portion surface so that upon disengagement of the stem from the hollow post and replacement of the closure portion the room deodorizer is ready for use.

* * * * *